Figure 1:
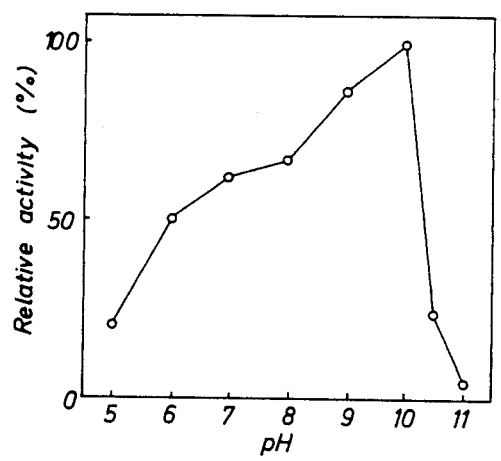

[54] NAD(P)H OXIDASE

[75] Inventors: Yoshio Yoshihama, Otsu; Asuka Kagaya, Nishinomiya; Susumu Matsui, Otsu; Akira Obayashi, Uji, all of Japan

[73] Assignee: Takara Shuzo Co., Ltd., Kyoto, Japan

[21] Appl. No.: 83,921

[22] Filed: Aug. 11, 1987

[30] Foreign Application Priority Data

Aug. 12, 1986 [JP] Japan .................. 61-188824
Nov. 28, 1986 [JP] Japan .................. 61-283240

[51] Int. Cl.$^5$ .................. C12N 9/06; C12N 9/02
[52] U.S. Cl. .................. 435/191; 435/189
[58] Field of Search .................. 435/189, 191

[56] References Cited

U.S. PATENT DOCUMENTS 4,186,052  1/1980  Roder et al. .................. 435/192

OTHER PUBLICATIONS

Chem. Abs. 123463s, Low et al, J. Bacteriol (1973), 116(1)346-354.
Derwent Abs. 85-118643/20 Hitachi (J60058069) 4-1985.
Biotech 86-09708 Evr. J. Biochem (1986), 156, 1, 149-155, Schmidt et al.
Japio Abst. 83-086099, Yokoyama et al, 5-1983, (J58086099).
Biochem 86-02985, Saeki et al, J. Biochem (1985), 98-6, 1433-1440.

Primary Examiner—Herbert J. Lilling
Attorney, Agent, or Firm—Wenderoth, Lind & Ponack

[57] ABSTRACT

NAD(P)H oxidase is disclosed having the following enzymological properties:
(1) Action
It oxidizes NADH or NADPH in the presence of oxygen to form NAD or NAD and hydrogen peroxide.

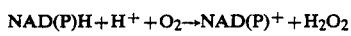

$$NAD(P)H + H^+ + O_2 \rightarrow NAD(P)^+ + H_2O_2$$

(2) Substrate specificity
It acts upon NADH and NADPH.
(3) Optimum pH
Its optimum pH lies in the range of about 9 to 10.
Also disclosed is a process for producing the NAD(P)H oxidase and a method for determining the quantity of substrate or enzyme activity in a sample solution by utilizing a reaction system forming NADH or NADPH.

1 Claim, 2 Drawing Sheets

NAD(P)H OXIDASE

The present invention relates to a novel NAD(P)H oxidase, a process for producing the same, and its use. More particularly, it relates to a novel NAD(P)H oxidase having its optimum pH on the alkaline side, to a process for producing the same, and to a method for determining the quantity of substrate or enzyme activity in a sample solution by using the same.

It has been reported that NAD(P)H oxidase, which acts upon nicotinamide-adenine dinucleotide of reduced form (hereinafter referred to as NADH) and nicotinamide-adenine dinucleotide phosphate of reduced form (hereinafter referred to as NADPH) to give hydrogen peroxide, is found in *Acholeplasma laidlawii* [European Journal of Biochemistry, 120, 329 (1981)] and in *Bacillus meqaterium* [Journal of Biochemistry, 98, 143 (1985)]. The enzyme obtained from these microorganisms has optimum pH at near neutrality.

NAD and NADP are coenzymes for various types of dehydrogenases. The quantity of substrate and enzyme activity in a sample solution can be estimated by quantitative determination of NADH or NADPH formed by the action of dehydrogenase. This technique is extensively used in clinical and food analyses.

NADH and NADPH are generally determined by measuring absorbance at 340 nm characteristic to these compounds or by colorimetric determination of formazan dye formed by reaction with a tetrazolium salt. The former method suffers from low sensitivty because the molecular extinction coefficients of NADH and NADPH are not so high, and the latter method has the problem that the formazan dye formed, which is sparingly soluble in water, tends to precipitate or attaches to the cell or tubing used.

These disadvantges can be avoided by the use of NAD(P)H oxidase, which oxidizes NADH or NADPH to form hydrogen peroxide, and by determining the amount of oxygen consumed or the amount of hydrogen peroxide formed. However, reactions of dehydrogenases are generally reversible, with the equilibrium being extensively shifted toward the side of NAD(P)H→NAD(P) at near neutrality, and hence it is difficult to determine the quantity of substrate or enzyme activity by coupling with NAD(P)H oxidase. On the alkaline side, on the other hand, the equilibrium shifts toward the side of NAD(P)→NAD(P)H. Under this condition, the coupling reaction will proceed easily, making possible high-sensitivity analysis by determination of the amount of oxygen consumed or the amount of hydrogen peroxide formed. Hence, there has been a great demand for the development of an NAD(P)H oxidase having its optimum pH on the alkaline side and of a method for substrate and enzyme activity determination using the same.

Thus the object of the present invention is to provide a novel NAD(P)H oxidase having its optimum pH on the alkaline side and to a simple, high-sensitivity and low-cost method for determining the quantity of susbstrate or enzyme activity in a sample solution by using the same.

The present invention relates to a novel NAD(P)H oxidase; more particularly, it relates to a novel NAD(P)H oxidase having its optimum pH on the alkaline side.

In another respect, the present invention relates to a process for producing said NAD(P)H oxidase.

In still another respect, the present invention relates to a method for determining the quantity of substrate and enzyme activity in a sample solution by using a novel NAD(P)H oxidase; more particularly, it relates to a method for determining teh quantity of substrate and enzyme activity in a sample solution by utilizing a reaction system forming NADH or NADPH, in which a novel NAD(P)H oxidase is used to measure the amount of oxygen consumed or the amount of hydrogen peroxide formed.

Figure 2:
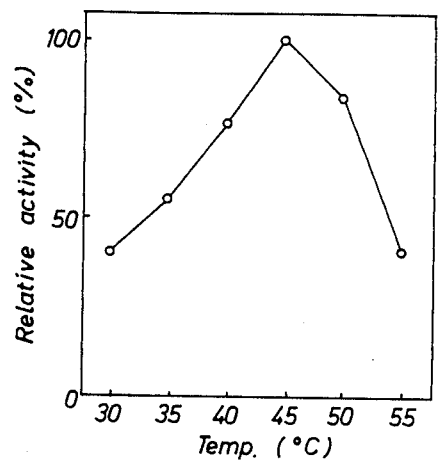
Figure 3:
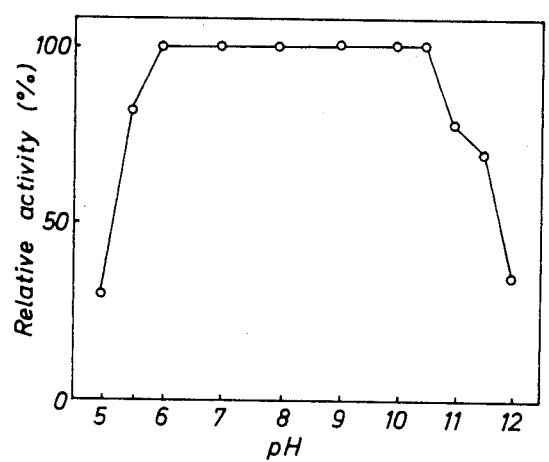
Figure 4:
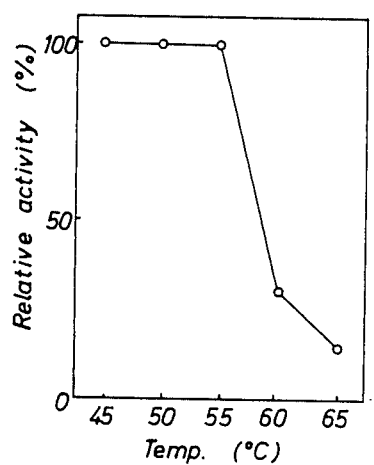
Figure 5:
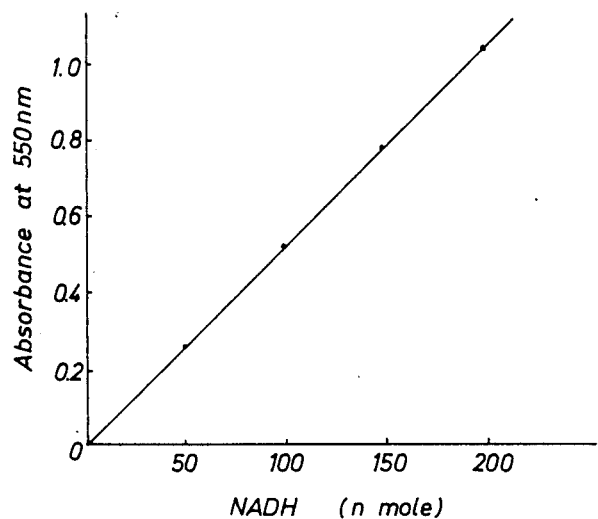
Figure 6:
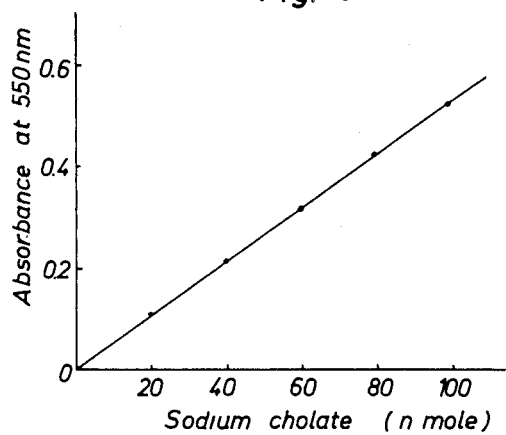

The invention will be explained below in more detail by referring partly to the accompanying drawings wherein: FIG. 1 is a graph illustrating the relationship between pH and the activity of the novel NAD(P)H oxidase of the present invention; FIG. 2 is a graph showing the relationship between temperature and the activity of the novel NAD(P)H oxidase of the present invention; FIG. 3 is a graph illustrating the pH range in which the enzyme of the present invention remains stable; FIG. 4 is a graph showing the thermostability of the enzyme of the present invention; FIG. 5 is a calibration curve used in Example 2 for the analytical method of the present invention, in which the absorbance at 550 nm is plotted against the amount of NADH; and FIG. 6 is a calibration curve used in Example 3 for the analytical method of the present invention, in which the absorbance at 550 nm is plotted against the amount of sodium cholate As a result of screening tests on NAD(P)H oxidases produced by microorganisms, we formerly found that *Brevibacterium ammoniagenes* and other species produce, inside their microbial cells, a stable NAD(P)H oxidase having its optimum pH on the alkaline side and studied its enzymological properties [Japanese Patent Application No.188824 (1986)]. This clearly differs from the NAD(P)H oxidases already reported in that it has the optimum pH on the alkaline side, and is therefore a novel NAD(P)H oxidase.

Any strains capable of producing the novel NAD(P)H oxidase may be used for the process for producing said novel NAD(P)H oxidase of the present invention. Preferred examples include *Brevibacterium ammoniagenes* IAM 1645 (FERM BP-1392), *Corynebacterium flaccumfaciens* AHU 1622, *Arthrobactor atrocyaneus* IAM 12339, *Micrococcus flavus* IFO 3242, *Pseudomonas aeruginosa* IAM 1156, *Acghromobactor parvulus* IFO 13182, *Agrobacterium radiobactor* IFO 12664, *Flavobacterium esteroaromaticum* IFO 3751 and *Streptomyces aureus* IAM 0092.

These strains may be grown in any type of culture medium so long as it allows production of the novel NAD(P)H oxidase of the present invention. Suitable nitrogen sources include yeast extract, peptone, meat extract, corn steep liquor, ammonium sulfate and ammonium chloride; and suitable carbon sources include glucose, molasses, glycerol, sucrose and sorbitol. In addition, inorganic salts or metal salts (e.g., phosphates, calcium salts and magnesium salts), vitamins and suitable growth factors may also be contained in the cluture medium.

These strains are generally cultivated at a temperature in the range from 20 to 40° C., preferably near at 30° C. The initial pH is generally in the range from 6 to 8, preferably near 7. The highest output of the novel NAD(P)H oxidase of the present invention is generally achieved by continuing cultivation with stirring and aeration for 10 to 30 hours. It is needless to say that such culture conditions be properly set depending on the particular strain and culture medium used so as to give the highest output of the novel NAD(P)H oxidase of the present invention.

Most of the novel NAD(P)H oxidase of the present invention thus produced is present inside the microbial cells. The culture broth obtained above is first subjected to solid-liquid separation, and the microbial cells thus separated are broken by a commonly used technique (e.g., ultrasonic treatment, treatment with an enzyme, and homogenizing), giving cell-free extract. Pure sample of the novel NAD(P)H oxidase, which shows a single band when measured by polyacrylamide gel electrophoresis, can be prepared from this cell-free extract by commonly used techniques, such as salting out, precipitation with an organic solvent, ion-exchange chromatography, adsorption chromatography, gel filtration and freeze-drying.

Enzymological properties of the novel NAD(P)H oxidase isolated from the culture broth of *Brevibacterium ammoniagenes* IAM 1645 (FERM BP-1392) in Example 1 are shown below.

(1) Action

The enzyme of the present invnetion oxidizes NADH and NADPH in the presence of oxygen to form NAD, NADP and hydrogen peroxide according to the equation given below.

$$NAD(P)H + H^+ + O_2 \rightarrow NAD(P)^+ + H_2O_2$$

(2) Substrate specificity

It acts upon NADH and NADPH.

(3) Optimum pH and pH Stability

Measurement using Britton-Robinson buffer solutions revealed that the enzyme of the present invention has its optimum pH at about 9 to 10 (FIG. 1). Separately, the enzyme of the present invention was treated at 37° C. for 60 minutes in Britton-Robinson buffer solutions of different pH values and the remaining activity was measured in each case. It was demonstrated that it is stable in the pH range from 6 to 10.5.

(4) Optimum Temperature and Thermostability

Measurement using a potassium phosphate buffer (pH 7.0) revealed that the optimum temperature of the novel NAD(P)H oxidase lies in the range of about 40° to 50° C. (FIG. 2). Separately, the enzyme of the present invention was treated in the same type of buffer as above at different temperatures for 10 minutes and the remaining activity was measured in each case. It was demonstrated that it is stable at temperatures up to 55° C. (FIG. 4).

Activity of the enzyme of the present invention was measured according to the procedure given below.

A solution prepared by mixing 1.0 ml of 0.3M potassium phosphate buffer (pH 7.0), 0.1 ml of 6mM NADH solution and 1.9 ml of distilled water was held at 37° C., 0.1 ml of the enzyme solution to be tested was added, the reaction was allowed to proceed at 37° C., and the decrease in absorbance at 340 nm was measured. The amount of enzyme that oxidizes 1 μmole NADH in one minute was taken as one unit.

The present invention employs a novel NAD(P)H oxidase having its optimum pH on the alkaline side, which is easily coupled with a dehydrogenase reaction, and hence allows high-sensitivity measurement. For example, when the novel NAD(P)H oxidase is used to determine the activity of lactate dehydrogenase (hereinafter abbreviated as LDH) in a sample solution through measurement of the amount of hydrogen peroxide formed, the following reaction system is established:

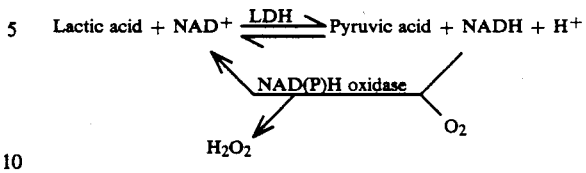

In this case, since the equilibrium of LHD reaction shifts toward the side of NADH→NAD+ near at neutrality, it is difficult to determine the activity of LDH from the amount of hydrogen peroxide formed by the action of NAD(P)H oxidase. Under alkaline conditions, on the other hand, the equilibrium shifts toward the side of NAD+→NADH, which allows the reaction catalyzed by the novel NAD(P)H oxidase to proceed extensively, and the LDH activity can thus be determined from the amount of hydrogen peroxide formed. Similarly, the amount of lactic acid in a sample solution can also be determined from the amount of hydrogen peroxide formed if LDH and the novel NAD(P)H oxidase are used under alkaline conditions. Thus the use of the novel NAD(P)H oxidase, which is stable and has favorable reactivity, is best suited for high-sensitivity analysis. The amount of hydrogen peroxide formed by the above enzymic reaction may be determined by the known fluorescence or chemiluminescence method.

The novel NAD(P)H oxidase of the present invention having its optimum pH on the alkaline side may be used in the form of a solution or in an immoblized form (fixed to a suitable carrier, such as glass beads and multilayer film). If the enzyme is fixed to an oxygen electrode, the quantity of substrate or enzyme activity in a sample solution can be determined by the amount of oxygen consumed. The present invention is characterized in that high-sensitivity measurement can be effected, that the novel NAD(P)H oxidase can be produced by microorganisms in large quantities at a low cost, and that the novel NAD(P)H oxidase produced by strains of Brevibacterium features high production efficiency and high stability, and thus provides a new method for determining substrate and enzyme activity useful in clinical examinations.

The analytical method of the present invention can be applied to any sample solution containing NADH or NADPH, including those solutions in which NADH or NADPH is formed as a result of enzymic reaction. Enumerated below are typical examples of the enzymic reactions which form NADH or NADPH and to which the method of the present invention is applicable for the determination of substrate and enzyme activity.

1. Alcohol dehydrogenase (EC 1.1.1.1)

$$Alcohol + NAD^{30} \rightleftarrows Aldehyde + NADH + H^+$$

2. Alcohol dehydrogenase (EC 1.1.1.2)

$$Alcohol + NADP^+ \rightleftarrows Aldehyde + NADPH + {}^+$$

3. Glycerol dehydrogenase (EC 1.1.1.6)

$$Glycerol + NAD^+ \rightleftarrows Dihydroxyacetone + NADH + H^+$$

4. L-lactate dehydrogenase (EC 1.1.1.27)

L-lactic acid + NAD⁺ ⇌ Pyruvic acid + NADH + H⁺

5. 3-Hydroxybutyrate dehydrogenase (EC 1.1.1.30)

D-3-Hydroxybutyric acid + NAD⁺ ⇌ Acetoacetic acid + NADH + H⁺

6. L-Malate dehydrogenase (EC 1.1.1.37)

L-Malic acid + NAD⁺ ⇌ Oxaloacetic acid + NADH + H⁺

7. L-Malate dehydrogenase (EC 1.1.1.40)

L-Malic acid + NADP⁺ ⇌ Pyruvic acid + $CO_2$ + NADPH + H⁺

8. Isocitrate dehydrogenase (EC 1.1.1.41)

Isocitric acid + NAD⁺ ⇌ 2-Oxoglutaric acid + $CO_2$ + NADH + H⁺

9. Isocitrate dehydrogenase (EC 1.1.1.42)

Isocitric acid + NADP⁺ ⇌ 2-Oxoglutaric acid + $CO_2$ + NADPH + H⁺

10. Glucose dehydrogenase (EC 1.1.1.47)

β-D-Gluopyranose + NAD(P)⁺ ⇌ D-Glucono-δ-lactone + NAD(P)H + H⁺

11. Galactose dehydrogenase (EC 1.1.1.48)

D-Galactofuranose NAD + NAD⁺ ⇌ D-Galactono-γ-lactone + NADH + H⁺

12. Glucose-6-phosphate dehydrogenase (EC 1.1.1.49)

D-Glucose-6-phosphate + NADP⁺ ⇌ D-Glucono-γ-lactone-6-phosphate + NADPH + H⁺

13. 3-Hydroxysteroid dehydrogenase (EC 1.1.1.50)

3-Hydroxysteroid + NAD(P)⁺ ⇌ 3-Oxosteroid + NAD(P)H + H⁺

14. Testosterone 17β-dehydrogenase (EC 1.1.1.63)

Testosterone + NAD⁺ ⇌ 4-Androstene-3,17-dione + NADH + H⁺

15. Testosterone 17β-dehydrogenase (EC 1.1.1.64)

Testosterone + NADP⁺ ⇌ 4-Androstene-3,17-dione + NADPH + H⁺

16. Galactose dehydrogenase (EC 1.1.1.120)

D-Galactofuranose + NADP⁺ ⇌ D-Galactono-γ-lactone + NADPH + H⁺

17. L-Fucose dehydrogenase (EC 1.1.1.122)

L-Fucopyranose + NAD⁺ ⇌ L-Fucono-1,5-lactone + NADH + H⁺

18. Formaldehyde dehydrogenase (EC 1.2.1.1)

Formaldehyde + Glutathione (reduced form) + NAD⁺ ⇌

S-Formylglutathione + NADH + H⁺

19. Formate dehydrogenase (EC 1.2.1.2)

Formic acid + NAD⁺ ⇌ $CO_2$ + NADH + H⁺

20. L-Alanine dehydrogenase (EC 1.4.1.1)

L-Alanine + $H_2O$ + NAD⁺ ⇌ Pyruvic acid + $NH_{4hu}$

+ NADH + H⁺

21. L-Glutamate dehydrogenase (EC 1.4.1.2)

L-glutamic acid + $H_2O$ + NAD⁺ ⇌ 2-Oxoglutaric acid

+ $NH_4^+$ + NADH + H⁺

22. L-Glutamate dehydrogenase (EC 1.4.1.3)

L-glutamic acid + $H_2O$ + NAD⁺ ⇌ 2-Oxoglutaric acid

+ $NH_4^+$ + NAD(PH)H + H⁺

The reactions shown above are presented by way of illustration and are not intended to limit the scope of the invention.

Intensive studies have led us to find that the quantity of substrate and enzyme activity can be simply determined at low cost by the use of a novel NAD(P)H oxidase having its optimum pH on the alkaline side. When the quantity of substrate in a sample solution is to be determined, a dehydrogenase that oxidized that substrate, NAD or NADP, and the novel NAD(P)H oxidase are added to the sample solution. An oxidized product of the substrate and NADH (or NADPH) are formed in the first reaction step, and the NADH (or NADPH) thus formed is then converted into NAD (or NADP) and hydrogen peroxide by the action of the novel NAD(P)H oxidase in the presence of oxygen. The same is true when determining the enzyme activity, giving NAD (or NADP) and hydrogen peroxide as the final reaction products. The amount of hydrogen peroxide thus formed can be determined by any known method, such as colorimetric, fluorescence, chemiluminescence and electrode methods, and an oxygen electrode may be used to determine the amount of oxygen consumed.

A typical colorimetric method for the determination of hydrogen peroxide is that using a peroxidase system. The most popular reagents employed in this system is the combination of 4-aminoantipyrine with phenol. However, phenol derivatives such as 2,4-dichlorophenol, 2,4-dibromophenol and 2,6-dichlorophenol, and aniline derivatives such as dimethylaniline, N-ethyl-N-(2-hydroxyethyl)-m-toluidine and N-ethyl-N-(2-hydroxy-3-sulfopropyl)-m-toluidine (hereinafter abbreviated as TOOS), may be used in place of phenol to further enhance the sensitivity. 4-Aminophenazone and 3-methylbenzothiazolinone hydrazone (MBTH) may also be used in place of 4-aminoantipyrine.

For the determination of hydrogen peroxide by fluorometry, methods are known in which homovanilic acid or p-hydroxyphenylacetic acid is converted to the corresponding fluorescent product by the action of hydrogen peroxide and peroxidase.

For the determination of hydrogen peroxide by the chemiluminescence method, a technique is known in which hydrogen peroxide is reacted with luminol and potassium ferricyanide to cause chemiluminescence.

There is no specific limitation upon the type of buffer solution used in the enzyme reaction of the present invention, but use of an alkaline buffer is preferable to facilitate the oxidation of NAD or NADP and the action of the novel NAD(P)H oxidase having its optimum pH on the alkaline side.

The novel NAD(P)H oxidase is used generally in an amount of 0.05 to 10 units, preferably in an amount of 0.1 to 1 unit. When determining the quantity of substrate in a sample solution, it is necessary to add a sufficient amount of dehydrogenase and to use NAD or NADP in an amount not smaller than that of substrate on a molar basis so that oxidation of the substrate (dehydrogenase reaction) will not be the rate-determining step of the overall reaction. Also when determining the enzyme activity, the substrate and NAD (or NADP) need be used in sufficient amounts so that the corresponding enzyme reaction will not be the rate-determining step of the overall reaction. The reaction is generally carried out at 20° to 40° C. for 1 to 30 minutes.

The process for producing the novel NAD(P)H oxidase of the present invention will be detailed in the following Examples, which are not intended to limit the scope of the invention.

EXAMPLE 1

A culture medium (100 ml) containing 1.0% glucose, 1.0% meat extract, 1.0% peptone, 0.1% KH2PO4 and 0.05% MgSO$_4$·7H$_2$O (pH 7.0) was placed in a 500ml conical flask and sterilized at 120° C. for 15 minutes, *Brevibacterium ammoniagenes* IAM 1645 (FERM BP-1392) was inoculated and shake culture was continued at 30° C. for 24 hours to give a seed culture.

A culture medium with the same composition as above (500 ml) was placed in a 2-liter conical flask and sterilized at 120° C. for 15 minutes, 20 ml of the seed culture obtained above was inoculated, and shake culture was continued at 30° C. for 15 hours. Wet microbial cells (68 g), obtained by centrifugal separation from five liters of the culture broth, were suspended in 150 ml of 30 mM potassium phosphate buffer (pH 7.0), the suspension was subjected to ultrasonic treatment to break the cell walls, the supernatant (crude enzyme solution) was dialyzed against 10 mM glycine-NaOH buffer solution (pH 9.0), and the dialyzate was allowed to pass through a DEAE-Sepharose (CL-6B) column (Pharmacia) previously equilibrated with the same buffer as above. The effluent showing the enzyme activity was adjusted to pH 10.0 by addition of a caustic soda solution, and allowed to pass through a Q-Sepharose (FF) column (Pharmacia) previously equilibrated with a 10 mM glycine-NaOH buffer (pH 10.0) to adsorb NAD(P)H oxidase. The adsorbed matter was eluted with NaCl solutions of 10mM to 1.0M concentrations by the linear concentration gradient technique. The active fractions collected were concentrated by means of a collodion bag, and the concentrate was subjected to gel filtration through a Sephacryl S-300 column (Pharmacia) previously equilibrated with 100 mM potassium phosphate buffer (pH 7.0), and the active fractions were collected, affording 50 mg of NAD(P)H oxidase. Its relative activity was 2.1 units/mg and the yield from the crude enzyme soluition was 42%.

EXAMPLE 2

A culture medium with the same composition as in Example 1 was dispersed in 500-ml conical flasks (100 ml in each), the flasks were sterilized by heating at 120° C. for 15 minutes, the strains listed in Table 1 were inoculated, and shake culture was continued at 30° C. for 24 hours. Each culture broth thus obtained was subjected to solid-liquid separation, and the microbial cells collected were suspended in 20 ml of 30 mM potassium phosphate buffer (ph 7.0). The suspension was then subjected to ultrasonic treatment and centrifugal separation, and the supernatant was measured for NAD(P)H oxidase activity. THe result is also shown in Table 1.

TABLE 1

| Strains | Activity (unit/ml) |
|---|---|
| *Brevibacterium ammoniagenes* IAM 1645 (FERM BP-1392) | 0.250 |
| *Corynebacterium flaccumfaciens* AHU 1622 | 0.122 |
| *Arthrobactor atrocyaneus* IAM 12339 | 0.092 |
| *Micrococcus flavus* IFO 3242 | 0.119 |
| *Pseudomonas aeruginosa* IAM 1156 | 0.107 |
| *Achromobactor parvulus* IFO 13182 | 0.107 |
| *Agrobacterium radiobactor* IFO 12664 | 0.100 |
| *Flavobacterium esteroaromaticum* IFO 3751 | 0.124 |
| *Strepromyces aureus* IAM 0092 | 0.068 |

EXAMPLE 3 (Determination of NADH)

(Compositions of Reagents)

| Solution R-1 | |
|---|---|
| Tris-HCl buffer (pH 9.0) | 50 mM |
| Novel NAD(P)H oxidase | 0.25 U/ml |
| Solution R-2 | |
| Phosphate buffer (pH 6.0) | 500 mM |
| 4-Aminoantipyrine | 2.4 mM |
| TOOS | 2.4 mM |
| Peroxidase (derived from horse radish; Sigma) | 24 U/ml |

A mixture of 2 ml of Solution R-1 with 10 μl of NADH solution (5, 10, 15 and 20 nM each) was held at 37° C. for 5 minutes to effect oxidation, 1 ml of Solution R-2 was added to each reaction mixture, and the absorbency at 550 nm was measured. A good linear relationship was observed between the amount of NADH used and the increase in absorbance at 550 nm as shown in FIG. 5.

EXAMPLE 4 (Determination of sodium cholate)

| (Compositions of Reagents) | |
|---|---|
| Solution R-1 | |
| Tris-HCl buffer (pH 9.0) | 50 mM |
| NAD | 1 mM |
| 3α-Hydroxysteroid dehydrogenase (derived from *Pseudmonas testosteroni*; Takara Shuzo) | 0.4 U/ml |
| Novel NAD(P)H oxidase | 0.8 U/ml |
| Solution R-2 | |
| Phosphate buffer (pH 6.0) | 500 mM |
| 4-Aminoantipyrine | 2.4 mM |
| TOOS | 2.4 mM |
| Peroxidase (derived from horse radish; Sigma) | 24 U/ml |

A mixture of 2 ml of Solution R-1 with 10 μl of sodium cholate solution (2, 4, 6, 8 and 10 mM each) was held at 37° C. for 5 minutes to effect oxidation, 1 ml of Solution R-2 was added to each reaction mixture, and the absorbance at 550 nm was measured. A good linear relationship was observed between the amount of sodium cholate used and the increase in absorbance at 550 nm as shown in FIG. 6.

EXAMPLE 5 (Determination of sodium cholate)

| (Composition of Reagent) | |
|---|---|
| Solution R-1 | |
| Tris-HCl buffer (pH 9.0) | 50 mM |
| NAD | 1 mM |
| 3α-Hydroxysteroid dehydrogenase | 0.4 U/ml |
| (derived from *Pseudmonas testosteroni*; Takara Shuzo) | |
| Novel NAD(P)H oxidase | 0.8 U/ml |

Solution R-1 (1.4 ml) was put in a closed cell equipped with a Clark oxygen electrode, 10 μl of sodium cholate solution (2, 4, 6, 8 and 10 mM each) was added, and the electrode was held at 37° C. for 5 minutes for stabilization. 10 mM sodium cholate solution (10 μl) was then added, and the amount of oxygen consumed was measured. A good linear relationship was observed between the amount of sodium cholate used and the amount of oxygen consumed.

Separately, the novel NAD(P)H oxidase was fixed to a film of acetylcellulose, this fixed enzyme was set in the same type of oxygen electrode, and a similar experiment to the above was conducted using this oxygen electrode. A similar satisfactory result was obtained in this case, too.

EXAMPLE 6 (Determination of lactate dehydrogenase activity)

| (Compositions of Reagents) | |
|---|---|
| Solution R-1 | |
| Glycine-NaOH buffer (pH 9.5) | 50 mM |
| Sodium L-lactate | 30 mM |
| NAD | 1 mM |

| -continued | |
|---|---|
| (Compositions of Reagents) | |
| Novel NAD(P)H oxidase | 0.8 U/ml |
| Solution R-2 | |
| Phosphate buffer (pH 6.0) | 500 mM |
| 4-Aminoantipyrine | 2.4 mM |
| TOOS | 2.4 mM |
| Peroxidase | 24 U/ml |
| (derived from horse radish; Sigma) | |

A mixture of 2 ml of Solution R-1 with 10 μl of lactate dehydrogenase solution (0.5, 1.0, 1.5, 2.0 and 2.5 mM each) was held at 37° C. for 5 minutes to effect oxidation, the reaction was terminated, 1 ml of Solution R-2 was added to each reaction mixture, and the absorbance at 550 nm was measured. A good linear relationship was observed between the amount of lactate dehydrogenase used and the increase in absorbance at 550 nm.

As may be apparent from the foregoing, the analytical method of the present invention is capable of specifically and quantitatively determining the quantity of substrate and enzyme activity in a sample solution with high sensitivity. The novel NAD(P)H oxidase of the present invention, which can be produced at a low cost by the action of microorganisms, serves as a useful reagent for clinical examinations.

What we claim is:

1. Novel NAD(P)H oxidase having the following enzymological properties:
   (1) Action
   It oxidizes NADH or NADPH in the presence of oxygen to form NAD or NADP and hydrogen peroxide.

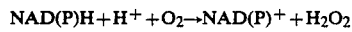

(2) Substrate specificity
   It acts upon NADH and NADPH.
   (3) Optimum pH
   Its optimum pH lies in the range of about 9 to 10.

* * * * *